United States Patent [19]

Dattagupta

[11] Patent Number: 4,968,602
[45] Date of Patent: Nov. 6, 1990

[54] SOLUTION-PHASE SINGLE HYBRIDIZATION ASSAY FOR DETECTING POLYNUCLEOTIDE SEQUENCES

[75] Inventor: Nanibhushan Dattagupta, New Haven, Conn.

[73] Assignee: Molecular Diagnostics, Inc., West Haven, Conn.

[21] Appl. No.: 442,423

[22] Filed: Nov. 21, 1989

Related U.S. Application Data

[63] Continuation of Ser. No. 927,613, Nov. 14, 1986, abandoned, which is a continuation-in-part of Ser. No. 836,360, Mar. 5, 1986, abandoned.

[51] Int. Cl.⁵ .............................................. C12Q 1/68
[52] U.S. Cl. ......................................... 435/6; 435/7; 435/29; 435/34; 435/803; 436/63
[58] Field of Search ....................... 435/6, 7, 803, 810, 435/29, 34; 935/78, 81; 436/501, 808, 63

[56] References Cited

U.S. PATENT DOCUMENTS

| 4,563,417 | 1/1986 | Albarella et al. ............... 935/78 X |
| 4,724,202 | 2/1988 | Dattagupta et al. . |
| 4,737,454 | 4/1988 | Dattagupta et al. ............. 935/77 X |
| 4,743,535 | 5/1988 | Carrico ........................... 935/78 X |

FOREIGN PATENT DOCUMENTS

| 040310 | 10/1985 | Australia . |
| 0070685 | 1/1983 | European Pat. Off. . |
| 0070687 | 1/1983 | European Pat. Off. . |
| 8301459 | 4/1983 | World Int. Prop. O. . |

OTHER PUBLICATIONS

Ranki et al., Gene, 21 (1983), 77–85.
Chem. Abs., vol. 108, No. 19, issued May 9, 1988, p. 361, 164418s, Dattagupta, N., "Preparation and Use ... the Reagents".
Dattagupta et al., Analytical Biochemistry 177, 85–89 (1989).
Dattagupta et al., Perspectives in Antiinfective Therapy (1989), pp. 241–247; Friedr. Vieweg & John, Wiesbaden.

Primary Examiner—Amelia Burgess Yarbrough
Assistant Examiner—S. Chambers
Attorney, Agent, or Firm—Sprung, Horn, Kramer & Woods

[57] ABSTRACT

A process for determining the presence of a particular nucleic acid sequence in a test sample comprising
(a) chemically modifying nucleic acids in the test sample either to introduce a label or a reactive site in a manner that supports their hybridizability,
(b) contacting under hybridization conditions the chemically modified sample nucleic acids with a hybridizable nucleic acid probe which either, when the sample nucleic acids have been modified to introduce a label, carrys a reactive site or, when the sample nucleic acids have been modified to introduce a reactive site, is labeled,
(c) contacting the solution resulting from step (b) with a immobilized form of a reactive partner to the reactive site to form a stable bond with the reactive site on the sample nucleic acids or the probe, respectively,
(d) separating the resulting immobilized fraction from the remaining solution, and
(e) determining the presence of the label in the separated immobilized fraction or a decrease in the label in the remaining solution.

15 Claims, 1 Drawing Sheet

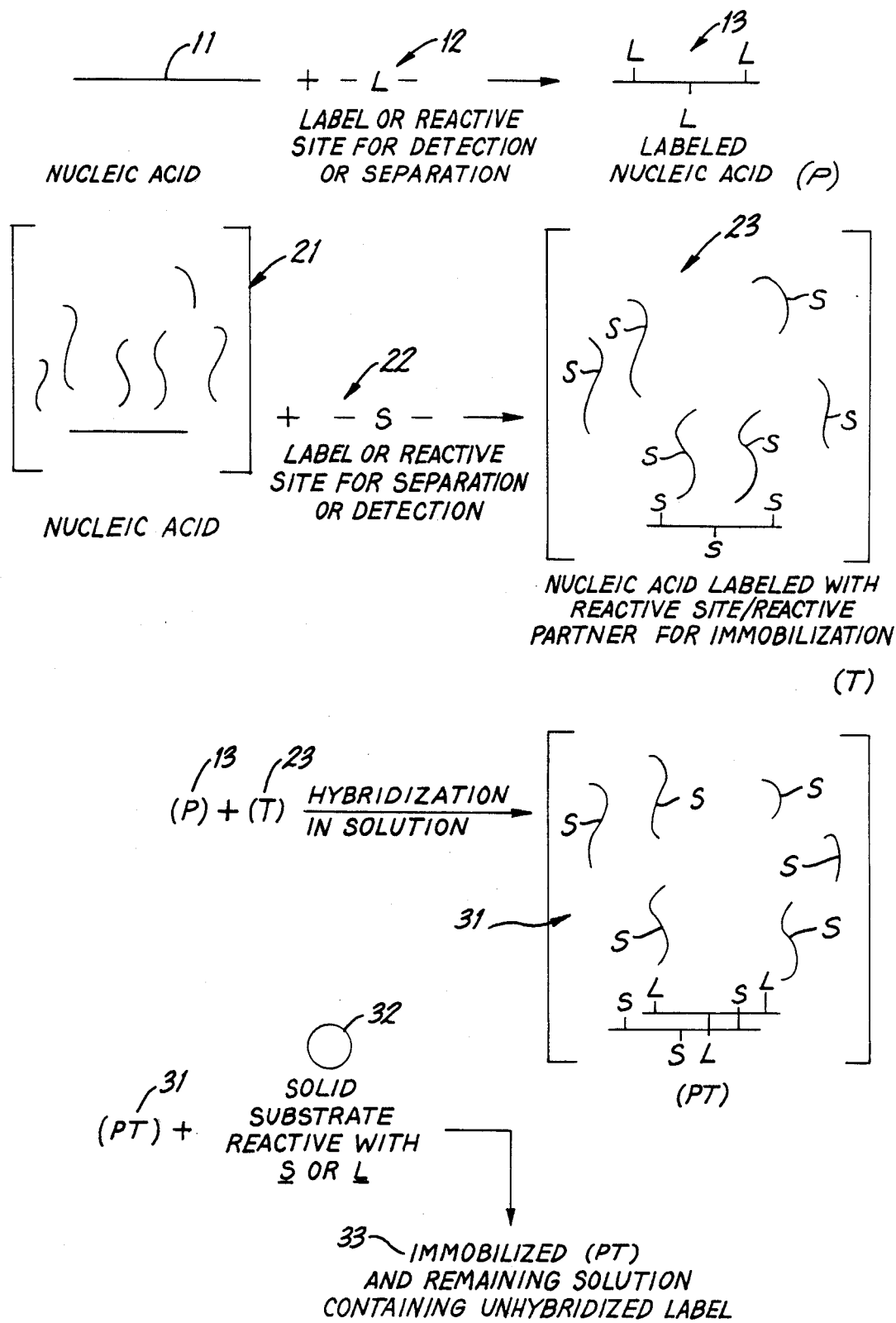

SOLUTION-PHASE SINGLE HYBRIDIZATION ASSAY FOR DETECTING POLYNUCLEOTIDE SEQUENCES

CROSS-REFERENCE TO RELATED APPLICATION

This application is a continuation of application Ser. No. 06/927,613, filed Nov. 14, 1986, now abandoned, which in turn was a continuation-in-part of application Ser. No. 06/836,360, filed Mar. 5, 1986, now abandoned.

BACKGROUND OF THE INVENTION

1. Field of the Invention

The present invention relates to a novel way of running tests to determine the presence of particular nucleic acid sequences in test samples and to novel probes useful therefor.

2. Background Information

The application of two non-overlapping DNA probes for hybridization has been disclosed in PCT patent application No. 83/01459, European patent application Nos. 0070687 and 0070685. PCT No. 83/01459 and 0070687 disclose the application of two non-overlapping hybridization probes for the detection of a particular polynucleotide sequence in a test sample. One of the probes is fixed to a solid support prior to hybridization. Although this method eliminates the problem of electrophoretic separation of nucleic acids before hybridization, the process is slow because of the heterogeneous phases utilized.

European publication No. 0070685 discloses a homogeneous phase two probe assay with a non-radiative transfer method. This method needs sophisticated equipment to monitor hybridization. The background cannot be eliminated because of brownian motion, some nonspecific reactions, and because the concentration of the unhybridized probes present in solution is always very high compared to the hybridized probes.

A heterogenous system involving two probes, one of which is immobilized, is described in application Ser. No. 815,694, filed Jan. 21, 1986, now abandoned in favor of application Ser. No. 07/052,634, filed May 20, 1987 and Ranki et al, Gene, 21, 77-85, (1983). The probes can be DNA, RNA, mixed nucleic acids or oligonucleotides. There are disclosed tests for particular nucleic acid sequences, such as that indicating sickle cell anemia, for example, by contacting the sample with two probes. The immobilized probe, otherwise identified as a separation probe, is immobilized on a support such as nitrocellulose. The other probe, identified as the detection probe, carries a label for ultimate assay. Both probes include different nucleic acid fragments, both complementary to a different portion of the test sequence if present in the test sample. The sample and probes are mixed, subjected to hybridizing conditions and, if the sample contains the right sequence, its nucleic acid will serve as a bridge between the two probes. Thereby the label of the labeled probe will become attached to the solid support. The support is removed and then "read" for the presence of the label.

The probes can be such that the label on the solid support will indicate either a positive or negative result with regard to the condition to be detected. In addition to sickle cell anemia, the test can be for any other genetic condition, e.g., thalassemia, Tay-Sachs, etc. An identical procedure can also be followed for the detection of bacteria or viruses in test samples.

While such process produces satisfactory results, it was desired to speed up the diagnostic process, without the disadvantages attending the homogeneous two probe assay noted hereinabove.

A homogeneous system involving two probes has been described in patent application Ser. No. 704,130, filed Feb. 21, 1985, now pending. This method uses two non-overlapping probes, one of which is labelled for detection and the other for the separation of the hybrid. The assay takes place in a homogeneous solution and the hybrid is subsequently separated by an immobilization reaction with a solid support and the separation probe.

Australian Patent Specification 40,310/85 concerns the use of an azide group to label probes. The Australian Patent Specification discloses the use of two probes involved in a single assay.

SUMMARY OF THE INVENTION

It is an object of the present invention to conduct assays for a particular nucleic acid sequence quickly by using only one probe.

It is another object of the present invention to conduct assays without the need for pure probes and samples.

These and other objects and advantages are realized in accordance with the present invention pursuant to which there is provided a homogeneous hybridization method coupled with a hybrid separation system. This procedure enables hybridization to occur rapidly and eliminates the background problem by selectively separating out the hybrids from the solution. The method requires only common laboratory equipment to assay the post hybridization products.

The diagnostic process takes place homogeneously, i.e., in solution. Moreover, the efficiency of the process of hybridization is higher in solution than in a heterogeneous system.

The above is accomplished by process for determining the presence of a particular nucleic acid sequence in a test sample comprising (a) chemically modifying nucleic acids in the test sample either to introduce a label or a reactive site in a manner that supports their hybridizability, (b) contacting under hybridization conditions the chemically modified sample nucleic acids with a hybridizable nucleic acid probe which either, when the sample nucleic acids have been modified to introduce a label, carries a reactive site or, when the sample nucleic acids have been modified to introduce a reactive site, is labeled, (c) contacting the solution resulting from step (b) with an immobilized form of a reactive partner to the reactive site to form a stable bond with the reactive site on the sample nucleic acids or the probe, respectively, (d) separating the resulting immobilized fraction from the remaining solution, and (e) determining the presence of the label in the separated immobilized fraction or a decrease in the label in the remaining solution.

The chemical modification can be accomplished by reaction with a photochemically reactive reagent (e.g., a nucleic acid binding ligand) comprising the label or the reactive site.

The concentration of the probe preferably is greater than the sample. For example, the probe can be in excess of the sample by at least 1,000 times in order to drive the reaction forward.

Preferably such reactable group (reactive site) in the probe is a binding site such as a biotin or hapten moiety which is capable of specific noncovalent binding with a binding substance such as avidin or an avidin which serves as the reaction partner.

The reactable group in an immobilized form is such that is attached to a solid support, for example, Sephadex gel, agarose, nitrocellulose paper and plastic.

The labeling of the sample or the probe can be accomplished by use of a detectable chemical group which can be radioactive, fluorescent, enzymatic or the like. Preferably the chemical modification of the sample nucleic acids, either to label or to introduce the substrate-reactable group, is accomplished by photochemical means.

The probe is combined with the test sample in a dilute aqueous solution. By utilizing suitable conditions of ionic strength, pH and temperature, if the proper components are present, hybridization will occur very rapidly. Then the immobilized reaction group is introduced and, after a suitable time to permit interaction of the reaction group and labelled sample, the immobile phase or fraction is removed, washed and the assay conducted, in known manner as described in application Ser. No. 511,063, supra.

BRIEF DESCRIPTION OF THE DRAWING

The drawing is a diagramatic representation of a method according to the present invention.

DETAILED DESCRIPTION OF THE INVENTION

The probe will comprise at least one single stranded base sequence substantially complementary to or homologous with the sequence to be detected. However, such base sequence need not be a single continuous polynucleotide segment, but can be comprised of two or more individual segments interrupted by non-homologous sequences. In addition, the homologous region of the probe can be flanked at the 3'- and 5'-termini by non-homologous sequences, such as those comprising the DNA or RNA of a vector into which the homologous sequence had been inserted for propagation. In any case, the probes as presented as analytical reagents will exhibit detectable hybridization at one or more points with sample nucleic acids of interest. Linear or circular single stranded polynucleotides can be used as probe elements, with major or minor portions being duplexed with a complementary polynucleotide strand or strands, provided that the critical homologous segment or segments are in single stranded form and available for hybridization with sample DNA or RNA. The probes can comprise DNA or RNA and can be of any convenient or desired length, ranging from 50 to a few kb, e.g., 10K bases, and including oligonucleotides having from about 4 to 50 bases. The preparation of a suitable probe for a particular assay is a matter of routine skill in the art.

The substrate-reactable group in the probe or sample nucleic acids, as the case may be, and the corresponding reactive partner on the immobilized phase will be referred to herein as a "reactive site/reactive partner pair".

Essentially any pair of substances can be used for this function of reactive site/reactive partner pair which exhibits an appropriate affinity for interacting to form a stable bond, that is a linking or coupling between the two which remains substantially intact during the subsequent assay steps, principally separation and detection steps. The bond formed may be a covalent bond or a noncovalent interaction, the latter being preferred especially when characterized by a degree of selectivity or specificity. In the case of such preferred bond formation, the reactive site will be referred to as a binding site and the reactable group as a binding substance with which it forms a covalent, noncovalent, commonly specific, bond or linkage.

In such preferred embodiment, the binding site can be present in a single-stranded hybridizable portion or in a single- or double-stranded nonhybridizable portion of the probe or can be present as a result of a chemical modification of the probe or sample nucleic acids. Examples of binding sites existing in the nucleotide sequence are where the probe comprises a promoter sequence (e.g., lac-promoter, trp-promoter) which is bindable by a promoter protein (e.g., bacteriophage promoters, RNA polymerase), or comprises an operator sequence (e.g., lac operator) which is bindable by a repressor protein (e.g., lac repressor) or comprises rare, antigenic nucleotides or sequences (e.g., 5-bromo or 5-iododeoxyuridine, Z-DNA) which are bindable by specific antibodies (see also British Patent Spec. No. 2,125,964). Binding sites introduced by chemical modification of the probe or sample polynucleotide are particularly useful and normally involve linking one member of a specific binding pair to the probe or sample nucleic acids. Useful binding pairs from which to choose include biotin/avidin (including egg white avidin and streptavidin), haptens and antigens/antibodies, carbohydrates/lectins, enzymes/inhibitors, and the like. Where the binding pair consists of a proteinaceous member and a nonproteinaceous member, it will be normally preferred to link the nonproteinaceous member to the probe or sample nucleic acids since the proteinaceous member may be unstable under the denaturing conditions of hybridization. Preferable systems involve linking the probe or sample nucleic acids with biotin or a hapten and employing immobilized avidin or anti-hapten antibody reagent, respectively.

An antibody reagent can be used in the present invention as described above as means for immobilizing a hapten or antigen-modified probe or sample nucleic acids. As used herein, antibody reagent refers to an immunologically derived binding substance having antibody binding activity and can be whole antibodies or fragments thereof, or aggregates or conjugates thereof, of the conventional polyclonal or monoclonal variety. When in the form of whole antibody, it can belong to any of the classes and subclasses of known immunoglobulins, e.g., IgG, IgM, and so forth. Any fragment of any such antibody which retains specific binding affinity for the binding site on the involved probe can also be employed, for instance, the fragments of IgG conventionally known as Fab, F(ab'), and F(ab')$_2$. In addition, aggregates, polymers, derivatives and conjugates of immunoglobulins or their fragments can be used where appropriate. The immunoglobulin source for the antibody reagent can be obtained in any available manner such as conventional antiserum and monoclonal techniques. Antiserum can be obtained by well-established techniques involving immunization of an animal, such as a mouse, rabbit, guinea pig or goat, with an appropriate immunogen. The immunoglobulins can also be obtained by somatic cell hybridization techniques, such resulting in what are commonly referred to as monoclonal antibodies, also involving the use of an appropriate immunogen.

A nucleic acid sample or a probe can be modified to have reactive

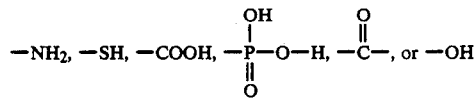

residues. This can be accomplished in a known manner. Using 5-allylamino UTP or 8-hexyl amino ATP and terminal deoxynucleotidyl transferase (TDT) -NH$_2$ residues can be introduced at the 3' end of the nucleic acid sample or probe. Using 4-thio UTP or 5-carboxy methyl UTP and TdT, -SH and -COOH residues can be introduced. Modified bases can also be introduced by nick translation. Alternatively a ligand can be covalently bound to the nucleic acid. The ligand can be the site of reaction. As for example a psoralen, an angelicin or azido ethidium with -NH$_2$ can be photochemically covalently bound to the nucleic acid sample or probe and then modified via the reaction site in the ligand. A restriction enzyme digested fragment usually produces a 5'-phosphorylated end. A carbonyl residue can be produced by oxidation of a terminal ribose residue (can be introduced via TdT reaction). All these site or sites can be present in one or multiple units per nucleic acid sample or probe. Once these residues are available known reactions can be used to form covalent linkage between these residues and an immobilization medium, e.g., solid particulate support having an -OH residue, or

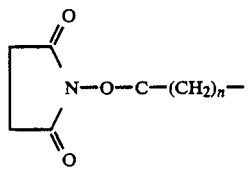

solid supoprt or HS—solid support, or

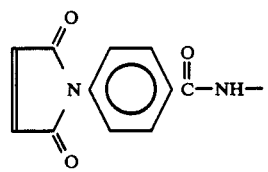

support, or

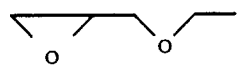

solid support, or OHC - solid support,

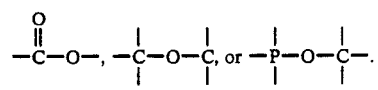

All these activated solid supports can be made by known reactions.

The reactive partner is used in the present assay in an immobilized form, that is, any suitable from that enables the reactive partner and any components of the reaction mixture that have become associated with it by hybridization and/or formation of the bond with the nucleic acid sample or probe, to be subsequently isolated or separated from the remaining mixture such as by centrifugation, filtration, chromatography, or decanting. A variety of compositions and configurations of the immobilized reactive partner will thus be evident and available to the worker in the field. In general such include attachment to a solid support, polymerization or attachment to a solid support, polymerization or attachment to a water dispersable material which can be subsequently precipitated or aggregated.

It is particularly preferred to employ a solid support to which the reactive partner is attached or fixed by covalent or noncovalent bonds, the latter including adsorption methods that provide for a suitably stable and strong attachment. The solid support can take a variety of shapes and compositions, including microparticles, beads, porous and impermeable strips and membranes, the interior surface of reaction vessels such as test tubes and microtiter plates, and the like. Means for attaching a desired reactive partner to a selected solid support will be a matter of routine skill to the worker in the field.

For example, where the reactive partner is a proteinaceous substance such as where avidin, an antibody reagent, or other binding protein is used as a binding substance for a binding site on the probe or sample nucleic acid, a large variety of methods are available in the literature for immobilizing such substances on solid supports (see *Methods in Enzymology*, Vol. 44(1976)). Proteins are commonly immobilized either by covalent coupling or by noncovalent adsorption. Noncovalent methods frequently employed are nonspecific adsorption to polystyrene beads or microparticles and to polyvinylchloride surfaces. Many covalent methods are used and a few involve cyanogen bromide activated agaroses and dextrans; glutaraldehyde activated nylons and polyacrylamides; and epoxides on acrylic and other supports. Antibodies of the IgG class can also be immobilized by the binding to immobilized forms of protein A. Non-specific adsorption on polystyrene latex particles can also be used.

There are a variety of methods that can be used in the present invention for determining the presence of the labeled sample or labeled probe in the separated immobilized fraction or in the remaining reaction solution in order to conclude the assay. One of ordinary skill in the art can choose from any conventional means for detecting the occurrence of hybridization between the detection probe and the sequence to be detected in the immobilized phase or its reduced presence in the reaction mixture. In general, the detection step will be based on the use of a labeled form of the sample or the probe, the use of a probe that forms a uniquely detectable hybrid with the sequence of interest, or via secondary reactions which can only be carried out when hybridization takes place, e.g., primer extension reaction.

The label for the sample or the probe will be a native characteristic of the polynucleotide or a substance which has a detectable physical, chemical, or electrical property. When a detectable labeling substance is introduced, it can be linked directly such as by covalent bonds to the sample or the probe or can be linked indirectly such as by incorporation of the ultimately detectable substance in a microcapsule or liposome which in turn is linked to the sample or the probe. It is particularly preferable that labeling can be conducted by a photochemical method.

Labeling materials have been well-developed in the field of immunoassays and in general most any label useful in such methods can be applied to the present invention. Particularly useful are enzymatically active groups, such as enzymes (see *Clin. Chem.*, 22, 1232, (1976), U.S. Reissue Pat. No. 31,006, and UK Patent No. 2,019,408), enzyme substrates (see U.S. Pat. No. 4,492,751), coenzymes (see U.S. Pat. Nos. 4,230,797 and 4,238,565), and enzyme inhibitors (see U.S. Pat. No. 4,134,792); fluorescers (see *Clin. Chem.*, 25, 353, (1979)); chromophores; luminescers such as chemiluminescers and bioluminescers (see U.S. Pat. No. 4,380,580); specifically bindable ligands such as biotin (see European Pat. Spec. No. 63,879) or a hapten (see PCT Publ. 83-2286); and radioisotopes such as $^3H$, $^{35}S$, $^{32}P$, $^{125}I$, and $^{14}C$. Such labels are detected on the basis of their own physical properties (e.g., fluorescers, chromophores and radioisotopes) or their reactive or binding properties (e.g., ligands, enzymes, substrates, coenzymes and inhibitors). For example, a cofactor-labeled species can be detected by adding the enzyme (or enzyme where a cycling system is used) for which the label is a cofactor and a substrate or substrates for the enzyme. A hapten or ligand (e.g., biotin) labeled species can be detected by adding an antibody to the hapten or a protein (e.g., avidin) which binds the ligand, tagged with a detectable molecule. Such detectable molecule can be some molecule with a measurable physical property (e.g., fluorescence or absorbance) or a participant in an enzyme reaction (e.g., see above list). For example, an enzyme can be used which acts upon a substrate to generate a product with a measurable physical property. Examples of the latter include, but are not limited to, beta-galactosidase, alkaline phosphatase and peroxidase.

Methods for preparing a labeled sample or a labeled probe used in the present invention are readily available from the prior art. When labeling samples or probes, synthetic approaches can be employed which are effective for modifying nucleic acids without substantially interfering with the ability of the labeled sample or the labeled probe to participate in hybridization, and labels can be selected which are sufficiently stable under the conditions to be used for hybridization to enable their subsequent detection. Single-stranded or double-stranded regions can be labeled as desired.

By way of example, the following approaches can be used in labeling samples or probes. Radiolabeled nucleotides can be incorporated into DNA samples or probes by methods such as nick translation and terminal labeling with terminal deoxynucleotidyl transferase. Radiolabeled nucleotides can be incorporated into RNA samples or probes during in vitro synthesis with DNA dependent RNA polymerase from bacteriophage SP6 using the "RIBOPROBE" DNA template system from Promega Biotec, Madison, Wis., U.S.A. The method of Langer et al (*Proc. Nat'l. Acad. Sci.*, 78, 6633, (1981)) can be used to couple biotin to the primary amine of 5-(3-amino)allyluridine and deoxyuridine triphosphates. These biotinylated nucleotides can be incorporated into double-stranded DNA by nick translation or added to the 3'-OH terminus with terminal deoxynucleotidyl transferase. Biotin can also be attached to the 3'-OH terminus of RNA through polyamine (Broker, T. R., *Nucl. Acids Res.*, 4, 363, (1978) and cytochrome C bridges (Sodja, A. and Davidson, N., *Nucl. Acids. Res.*, 5, 385, (1978)). Direct coupling of protein labels to samples or probes can be accomplished by the method of Renz (*EMBO Journal*, 2, 817, (1982)) who coupled $^{125}I$-histones to denatured DNA with glutaraldehyde. Enzymes such as peroxidase and alkaline phosphatase can be linked to DNA samples or probes by means of similar chemistry (Renz and Kurz, *Nucl. Acids Res.*, 12, 3435, (1984)). Other chemistries for end-labeling DNA samples or probes include that described by Eshaghpour et al (*Nucl. Acids Res.*, 7, 1485, (1979)). One or more 4-thiouridine residues can be introduced on the 3'-OH ends of DNA and the thiols reacted with various electrophilic low molecular weight reagents This chemistry can be used to attach various haptens to DNA samples or probes. Labeling with the hapten N-acetoxy-N-2-acetylaminofluorene is described by Tchen et al, (*Proc. Nat'l. Acad. Sci.*, 81, 3466, (1984)). DNA and RNA samples or probes can be reacted with N-acetoxy-N-2-acetylaminofluorene to yield an adduct having N-2-acetylaminofluorene residues attached at the 8-carbon of guanine. The covalently modified DNA can be detected with antibody raised against the N-acetoxy-N-2-acetylaminofluorene residue. The method of Hu and Messing, *Gene*, 17, 271, (1982) can be used for adding labels to probes cloned into single-stranded M13 vectors. A universal primer, complementary to the region 5' to the cloning site, initiates DNA synthesis complementary to the M13 strand downstream from the probe sequence. Since the DNA polymerase will incorporate radioactive nucleotide triphosphates and biotin 5-(3-aminoallyl) deoxyuridine triphosphate into the new strand, those labels can be attached to the vector away from the probe sequence. The double-stranded portion can also be modified by reaction with 8-azidoethidium.

Another particularly preferred approach to the detection step involves the use of a probe system wherein the hybrid formed between the polynucleotide sequence of interest and the probe is antigenically distinct from its individual single-strands. One is thus enabled to detect the presence of the probe in the immobilized fraction containing hybridized probe by adding an antibody reagent as discussed above that is selective for binding such hybrids. Preferred antibody reagents will be those that are selective for binding double-stranded nucleic acids over single-stranded nucleic acids, e.g., those which selectively bind (i) DNA.RNA or RNA.RNA hybrids or (ii) intercalation complexes. In the first instance, an antibody reagent selective for binding DNA.RNA hybrids will be useful where one of the probe and the sequence to be detected is DNA and the other is RNA, and in either case of course the probe will be the same RNA or DNA as the sequence to be detected. One can use an antibody reagent selective for finding RNA.RNA hybrids where both the probe and the sequence of interest are RNA and the probe is DNA. In the case of intercalation complexes, the assay will be designed so that the hybrids formed between the probe and the sequence of interest will comprise a nucleic acid intercalator bound thereto in the form of intercalation complexes.

Immunogens for stimulating antibodies specific for RNA.DNA hybrids can comprise homopolymeric or heteropolymeric polynucleotide duplexes. Among the possible homopolymer duplexes particularly preferred is poly(rA).poly(dT) (Kitagawa and Stollar Mol. Immuno., 19, 413 (1982)). However, in general heteropolymer duplexes will be preferably used and can be prepared in a variety of ways, including transcription of $\phi$X174 virion DNA with RNA polymerase (Nakazato, Biochem., 19, 2835 (1980)). The selected RNA.DNA duplexes are adsorbed to a methylated protein, or otherwise linked to a conventional immunogenic carrier material, such as bovine serum albumin, and injected into the desired host animal (see also Stollar, Meth. Enzymol., 70, (1980)). Antibodies to RNA.RNA duplexes can be raised against double-stranded RNAs from viruses such as retrovirus or Fiji disease virus which infects sugar cane, among others. Also, homopolymer duplexes such as poly(rI).poly(rC) or poly(rA).poly(rU), among others, can be used for immunization as above.

Antibodies to intercalation complexes can be prepared against an immunogen which will usually comprise an ionic complex between a cationic protein or protein derivative (e.g., methylated bovine serum albumin) and the anionic intercalator-nucleic acid complex. Ideally, the intercalator will be covalently coupled to the double-stranded nucleic acid. Alternatively, the intercalator-nucleic acid conjugate can be covalently coupled to a carrier protein. The nucleic acid portion of the immunogen can comprise the specific paired sequences found in the assay hybrid or can comprise any other desirable sequences, since the specificity of the antibody will generally not be dependent upon the particular base sequences involved.

In other instances where an antibody reagent selective for intercalation complexes is employed in the detection system, a variety of intercalator compounds can be involved. In general it can be said that the intercalator compound preferably is a low molecular weight, planar, usually aromatic, but sometimes polycyclic, molecule capable of binding with doublestranded nucleic acids, e.g., DNA.DNA, DNA.RNA, or RNA.RNA duplexes, usually by insertion between base pairs. The primary binding mechanism will usually be noncovalent, with covalent binding occurring as a second step where the intercalator has reactive or activatable chemical groups which will form covalent bonds with neighboring chemical groups on one or both of the intercalated duplex strands. The result of intercalation is the spreading of adjacent base pairs to about twice their normal separation distance, leading to an increase in molecular length of the duplex. Further, unwinding of the double helix of about 12 to 36 degrees must occur in order to accomodate the intercalator. General reviews and further information can be obtained from Lerman, J., Mol. Biol., 3, 18 (1961); Bloomfield et al, "Physical Chemistry of Nucleic Acids", Chapter 7, pp. 429–476, Harper and Rowe, N.Y. (1974); Waring, Nature, 219, 1320 (1968); Hartmann et al, Angew. Chem., Engl. Ed., 7, 693 (1968); Lippard, Accts. Chem. Res., 11, 211, (1978); Wilson, Intercalation Chemistry, (1982), 445; and Berman et al, Ann. Rev. Biophys. Bioeng., 20, 87 (1981). Exemplary of intercalators are acridine dyes, e.g. acridine orange, the phenanthridines, e.g., ethidium, the phenazines, furocoumarins, phenothiazines, and quinolines.

The intercalation complexes are formed in the assay medium during hybridization by use of a probe which has been modified in its complementary, single-stranded region to have the intercalator chemically linked thereto such that upon hybridization the intercalation complexes are formed. Essentially any convenient method can be used to accomplish such linkage. Usually, the linkage is formed by effecting intercalation with a reactive, preferably photoreactive intercalator, followed by the linking reaction. A particularly useful method involves the azidointercalators. Upon exposure to ultraviolet or visible light, the reactive nitrenes are readily generated. The nitrenes of arylazides prefer insertion reactions over their rearrangement products (see White et al, Methods in Enzymol., 46, 644 (1977)). Representative azidointercalators are 3-azidoacridine, 9-azidoacridine, ethidium monoazide, ethidium diazide, ethidium dimer azide (Mitchell et al, JACS, 104, 4265 (1982)) 4-azido-7-chloroquinoline, and 2-azidofluorene. Other useful photoreactable intercalators are the furocoumarins which form (2+2) cycloadducts with pyrimidine residues. Alkylating agents can also be used such as bischloroethylamines and epoxides or aziridines, e.g., aflatoxins, polycyclic hydrocarbon epoxides, mitomycin, and norphillin A. The intercalator-modified duplex is then denatured to yield the modified single-stranded probe.

The detection of antibody reagent that binds to the antigenically distinct hybrid formed between the detection probe and the sequence of interest can proceed in any conventional manner. For example, one can employ antibody reagent which has been labeled with any detectable chemical group as discussed above. The preparation of labeled antibodies is described extensively in the literature. Incorporation of $^{125}$I-label can be accomplished by the method of Bolton and Hunter, Biochem. J., 133, 529 (1972). Ishikawa et al, J. Immunoassay, 4, 209 (1982) have outlined several different methods for coupling various enzymes to antibodies. Yoshitake et al, Eur. J. Biochem., 101, 395 (1979) have described a method for using maleimides to couple glucose oxidase to antibody. Alkaline phosphatase can be coupled to antibody with glutaraldehyde [Voller et al, Bull. World Health Organ., 53, 55 (1976)]. Antibodies can be labeled with fluorescein by the method of Blakeslee and Baines, J. Immunol. Meth., 13, 305 (1976). Chemiluminescent labels can be introduced by the method of Schroeder et al, Clin. Chem., 27, 1378 (1981). Alternatively, the antibody reagent can be detected based on a native property such as its own antigenicity. A labeled anti-(antibody) antibody will bind to the primary antibody reagent where the label for the second antibody is any conventional label as above. Further, antibody can be detected by complement fixation or the use of labeled protein A, as well as other techniques known in the art for detecting antibodies.

The test sample to be assayed can be any medium of interest, and will usually be a liquid sample of medical, veterinary, environmental, nutritional, or industrial significance. Human and animal specimens and body fluids particularly can be assayed by the present method, including urine, blood (serum or plasma), milk, cerebrospinal fluid, sputum, fecal matter, lung aspirates, throat swabs, genital swabs and exudates, rectal swab, and nasopharnygal aspirates. Where the test sample obtained from the patient or other source to be tested contains principally double-stranded nucleic acids, such as contained in cells, the sample will be treated to denature the nucleic acids, and if necessary first to release acids from cells.

One aspect of the present invention involves the labeling of nucleic acids in the test sample or their chemical modification to introduce the reactive site for subsequent immobilization either in whole cells, lysates, or purified nucleic acids. A surprising feature of the invention is the efficient labeling or reactive site-modification of whole cells. One method of labeling or reactive site-modification is a photochemical reaction using DNA binding ligands as carriers for detectable labels. The clinical sample is processed for the separation of infectious cells, e.g., by centrifugation of urine or blood from the patient and then the photochemical reagent is added and the mixture is irradiated to produce labeled or reactive site-modified test samples, as the case may be.

The nucleic acid is labeled or modified by means of photochemistry, employing a photoreactive nucleic acid-binding ligand, e.g., an intercalator compound such as a furocoumarin or a phenanthridine compound or a non-intercalator compound such as netropsin, distamycin, Hoechst 33258 and bis-benzimidazole to link the nucleic acid to a label which can be "read" or assayed in conventional manner, including fluorescence detection, or a reactive site that can be the means for subsequent immobilization as described above. The end product is thus a labeled or modified nucleic acid probe comprising (a) a nucleic acid component, (b) an intercalator or other nucleic acid-binding ligand photochemically linked to the nucleic acid component, and (c) a label or reactive site chemically linked to (b).

The novel photochemical method provides more favorable reaction conditions than the usual chemical coupling method for biochemically sensitive substances. By using proper wavelengths for irradiation, DNA, RNA and proteins can be modified without affecting the native structure of the polymers. The nucleic acid-binding ligand, hereinafter exemplified by an intercalator, and label or reactive site can first be coupled and then photoreacted with the nucleic acid or the nucleic acid can first be photoreacted with the intercalator and then coupled to the label or reactive site. A general scheme for coupling a nucleic acid, exemplified by double-stranded DNA, to a label or reactive site exemplified by a hapten is as follows:

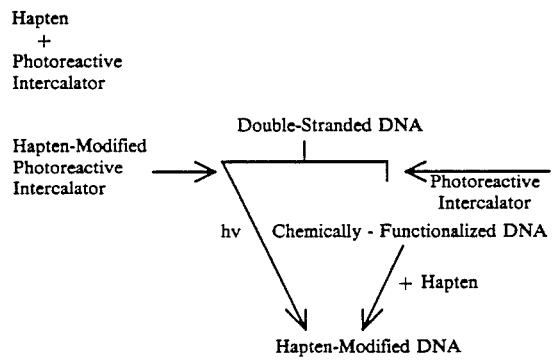

Where the hybridizable portion of the nucleic acid is in a double stranded form, such portion is then denatured to yield a hybridizable single stranded portion. Alternatively, where the labeled or modified nucleic acid, e.g., RNA or DNA comprises the hybridizable portion already in single stranded form, such denaturization can be avoided if desired To produce specific and efficient photochemical products, it is desirable that the nucleic acid component and the photoreactive intercalator compound be allowed to react in the dark in a specific manner.

For coupling to nucleic acid, aminomethyl psoralen, aminomethyl angelicin and amino alkyl ethidium or methidium azides are particularly useful compounds. They bind to double-stranded nucleic acid and only the complex produces photoadduct. In the case where labeled or reactive site-modified double-stranded nucleic acid must be denatured in order to yield a hybridizable single stranded region, conditions are employed so that simultaneous interaction of two strands of nucleic acid with a single photoadduct is prevented. It is necessary that the frequency of modification along a hybridizable single stranded portion of the probe or sample not be so great as to substantially prevent hybridization, and accordingly there preferably will be not more than one site of modification per 25, more usually 50, and preferably 100, nucleotide bases. Angelicin derivatives are superior to psoralen compounds for monoadduct formation. If a single-stranded nucleic acid is covalently attached to some extra double-stranded nucleic acid, use of phenanthridium and psoralen compounds is desirable since these compounds interact specifically to double-stranded nucleic acid in the dark. The chemistry for the synthesis of the coupled reagents to modify nucleic acids for labeling or introducing a reactive site, described more fully hereinbelow, is similar for all cases.

The nucleic acid component can be singly or doubly stranded DNA or RNA or fragments thereof such as are produced by restriction enzymes or even relatively short oligomers.

The nucleic acid-binding ligands of the present invention used to link the nucleic acid component to the label or reactive site can be any suitable photoreactive form of known nucleic acid-binding ligands. Particularly preferred nucleic acid-binding ligands are intercalator compounds such as the furocoumarins, e.g., angelicin (isopsoralen) or psoralen or derivatives thereof which photochemically will react with nucleic acids, e.g., 4'-aminomethyl-4,5'-dimethyl angelicin, 4'-aminomethyl-trioxsalen (4'-aminomethyl- 4,5',8-trimethyl-psoralen, 3-carboxy-5- or -8-amino- or -hydroxy-psoralen, as well as mono- or bis-azido aminoalkyl methidium or ethidium compounds. Photoreactive forms of a variety of other intercalating agents can also be used as exemplified in the following table:

| Intercalator Classes and Representative Compounds | Literature References |
|---|---|
| A. Acridine dyes | Lerman, J. Mol. Biol. 3:18(1961); Bloomfield et al, "Physical Chemistry of Nucleic Acids", Chapter 7, pp. 429-476, Harper and Rowe, NY(1974) |
| proflavin, acridine orange, quinacrine, acriflavine | Miller et al, Biopolymers 19:2091(1980) |
| B. Phenanthridines | Bloomfield et al, supra Miller et al, supra |
| ethidium | |
| coralyne | Wilson et al, J. Med. |

-continued

| Intercalator Classes and Representative Compounds | Literature References |
|---|---|
| ellipticine, ellipticine cation and derivatives | Chem. 19:1261(1976) Festy et al, FEBS Letters 17:321(1971); Kohn et al, Cancer Res. 35:71(1976); LePecq et al, PNAS (USA)71: 5078(1974); Pelaprat et al, J. Med. Chem. 23:1330(1980) |
| C. Phenazines | Bloomfield et al, supra |
| 5-methylphenazine cation | |
| D. Phenothiazines chlopromazine | " |
| E. Quinolines chloroquine quinine | " |
| F. Aflatoxin | " |
| G. Polycyclic hydrocarbons and their oxirane derivatives | " |
| 3,4-benzpyrene benzopyrene diol epoxide, 1-pyrenyl-oxirane | Yang et al, Biochem. Biophys. Res. Comm. 82:929(1978) |
| benzanthracene-5,6-oxide | Amea et al, Science 176:47(1972) |
| H. Actinomycins actinomycin D | Bloomfield et al, supra |
| I. Anthracyclinones β-rhodomycin A daunamycin | " |
| J. Thiaxanthenones miracil D | " |
| K. Anthramycin | " |
| L. Mitomycin | Ogawa et al, Nucl. Acids Res., Spec. Publ. 3:79(1977); Akhtar et al, Can. J. Chem. 53:2891(2975) |
| M. Platinium Complexes | Lippard, Accts. Chem. Res. 11:211(1978) |
| N. Polyintercalators echinomycin | Waring et al, Nature 252:653(1974); Wakelin, Biochem. J. 157:721(1976) |
| quinomycin triostin BBM928A tandem | Lee et al, Biochem. J. 173:115(1978): Huang et al, Biochem. 19: 5537(1980): Viswamitra et al, Nature 289: 817(1981) |
| diacridines | LePecq et al, PNAS (USA)72:2915(1975): Carrellakis et al, Biochim. Biophys. Acta 418:277(1976); Wakelin et al, Biochem 17:5057(1978); Wakelin et al, FEBS Lett. 104:261(1979); Capelle et al, Biochem. 18:3354 (1979); Wright et al, Biochem. 19:5825(1980); Bernier et al, Biochem. J. 199:479 (1981); King et al, Biochem. 21:4982 (1982) |
| ethidium dimer | Gaugain et al, Biochem. 17:5078(1978); Kuhlman et al, Nucl. Acids Res. 5:2629(1978); Marlcovits et al, Anal. Biochem. 94:259(1979): Dervan et al, JACS 100:1968(1978); Dervan et al, JACS 101:3664(1979). |

-continued

| Intercalator Classes and Representative Compounds | Literature References |
|---|---|
| ellipticene dimers and analogs | Debarre et al, Compt. Rend. Ser. D. 284: 81(1977); Pelaprat et al, J. Med. Chem. 23:1336(1980) |
| heterodimers | Cain et al, J. Med. Chem. 21:658(1978); Gaugain et al, Biochem. 17:5078(1978) |
| trimers | Hansen et al, JCS Chem. Comm. 162(1983); Atnell et al, JACS 105:2913(1983) |
| O. Norphillin A | Loun et al, JACS 104: 3213(1982) |
| P. Fluorenes and fluorenones fluorenodiamines | Bloomfield et al, supra Witkowski et al, Wiss. Beitr.-Martin-Luther-Univ. Halle Wittenberg, 11(1981) |
| Q. Furocoumarins angelicin | Venema et al, MGG, Mol. Gen. Genet. 179;1 (1980) |
| 4,5'-dimethylangelicin | Vedaldi et al, Chem.-Biol. Interact. 36: 275(1981) |
| psoralen | Marciani et al, Z. Naturforsch B 27(2): 196(1972) |
| 8-methoxypsoralen | Belognzov et al, Mutat. Res. 84:11(1981); Scott et al, Photochem. Photobiol. 34:63(1981) |
| 5-aminomethyl-8-methoxypsoralen | Hansen et al, Tet. Lett. 22:1847(1981) |
| 4,5,8-trimethylpsoralen | Ben-Hur et al, Biochem. Biophys. Acta 331:181(1973) |
| 4'-aminomethyl-4,5,8-trimethylpsoralen | Issacs et al, Biochem. 16:1058(1977) |
| xanthotoxin | Hradecma et al, Acta Virol. (Engl. Ed.) 26: 305(1982) |
| khellin | Beaumont et al, Biochim. Biophys. Acta 608:1829(1980) |
| R. Benzodipyrones | Murx et al, J. Het. Chem. 12:417(1975); Horter et al, Photo-chem. Photobiol. 20: 407(1974) |
| S. Monostral Fast Blue | Juarranz et al, Acta Histochem. 70:130 (1982) |

Particularly useful photoreactive forms of such intercalating agents are the azidointercalators. Their reactive nitrenes are readily generated at long wavelength ultraviolet or visible light and the nitrenes of arylazides prefer insertion reactions over their rearrangement products [see White et al, *Methods in Enzymol.*, 46, 644, (1977)]. Representative azidointercalators are 3-azidoacridine, 9-azidoacridine, ethidium monoazide, ethidium diazide, ethidium dimer azide [Mitchell et al, *JACS*, 104, 4265, (1982)], 4-azido-7-chloroquinoline, and 2-azidofluorene. Other useful photoreactable intercalators are the furocoumarins which form [2+2]cycloadducts with pyrimidine residues. Alkylating agents can also be used such as bischloroethylamines and epoxides or aziridines, e.g., aflatoxins, polycyclic hydrocarbon epoxides, mitomycin, and norphillin A.

The label or reactive group will be linked to the intercalator compound by direct chemical linkage such as involving covalent bonds, or by indirect linkage such as by the incorporation of the label or reactive group in a microcapsule or liposome which in turn is linked to the intercalator compound. Methods by which the label or reactive group is linked to the intercalator compound are essentially known in the art and any convenient method can be used to perform the present invention.

Advantageously the intercalator compound is first combined with the label or reactive group chemically and thereafter combined with the nucleic acid component. For example, since biotin carries a carboxyl group it can be combined with a furocoumarin by way of amide or ester formation without interfering with the photochemical reactivity of the furocoumarin or the biological activity of the biotin, e.g.,

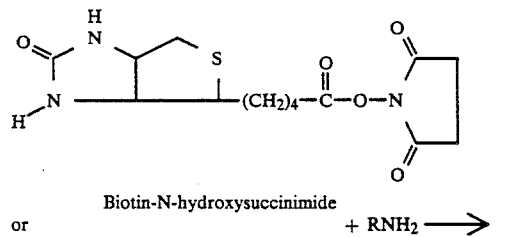

Biotin-N-hydroxysuccinimide or    + RNH₂ ⟶

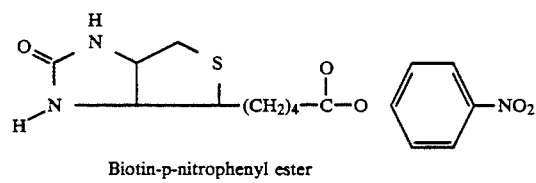

Biotin-p-nitrophenyl ester

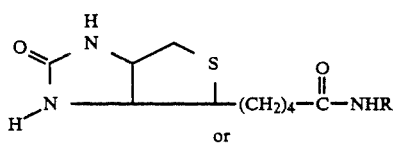

or

Biotin + ROH —carbodiimide→ Biotin CO OR

By way of example,

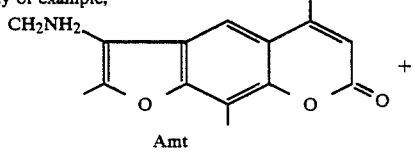

Amt

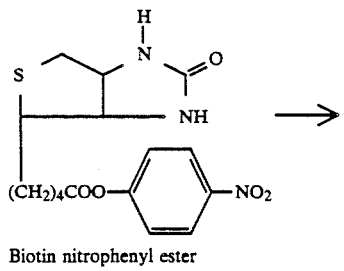

Biotin nitrophenyl ester

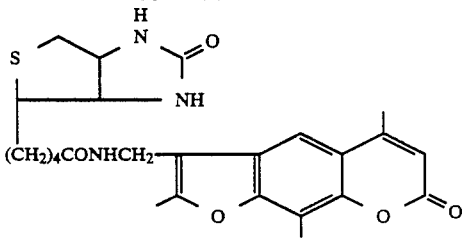

Other aminomethylangelicin, psoralen and phenanthridium derivatives can be similarly reacted, as can phenanthridium halides and derivatives thereof such as aminopropyl methidium chloride, i.e.

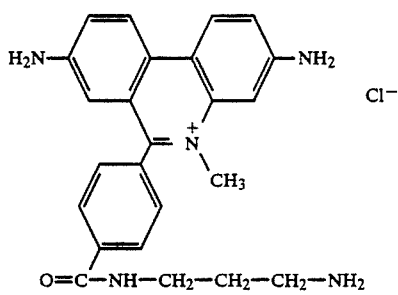

[see Hertzberg et al, *J. Amer. Chem. Soc.*, 104, 313, (1982)].

Alternatively a bifunctional reagent such as dithiobis succinimidyl propionate or 1,4-butanediol diglycidyl ether can be used directly to couple the photochemically reactive molecule with the label where the reactants have alkyl amino residues, again in a known manner with regard to solvents, proportions and reaction conditions. Certain bifunctional reagents, possibly glutaraldyde may not be suitable because, while they couple, they may modify the nucleic acid and thus interfere with the assay. Routine precautions can be taken to prevent such difficulties. The particular sequence in making the labeled or reactive site-modified nucleic acid can be varied. Thus, for example, an amino-substituted psoralen can first be photometrically coupled with a nucleic acid, the product having pendant amino groups by which it can be coupled to the label or reactive site. Alternatively, the psoralen can first be coupled to a label or a reactive site and then to the nucleic acid.

The spacer chain length between the nucleic acid-binding ligand and the label or reactive site can be extended via hydrocarbon or peptide. A typical example involves extending an 8-hydroxy psoralen derivative with an alkyl halide, according to the method described by J. L. DeCout and J. Lhomme, *Photochemistry Photobiology*, 37, 155–161, (1983). The haloalkylated derivative is then reacted either with thiol or amines to produce the reactive residue, as has been described by W. A. Saffran et al., *Proc. Natl. Acad. Sci. U.S.A.*, 79, 4594, (1982).

If the label is an enzyme, for example, the product will ultimately be placed on a suitable medium and the extent of catalysis will be determined. Thus, if the enzyme is a phosphatase the medium could contain nitrophenyl phosphate and one would monitor the amount of nitrophenol generated by observing the color. If the enzyme is a beta-galactosidase the medium can contain o-nitrophenyl-D-galacto-pyranoside which also will liberate nitrophenol.

Denaturation of nucleic acids is preferably accomplished by heating in boiling water or alkali treatment (e.g., 0.1 N sodium hydroxide), which if desired, can simultaneously be used to lyse cells. Also, release of nucleic acids can, for example, be obtained by mechanical disruption (freeze/thaw, abrasion, sonication), physical/chemical disruption (detergents such as "TRITON", "TWEEN", sodium dodecylsulfate, alkali treatment osmotic shock, or heat), or enzymatic lysis (lysozyme, proteinase K, pepsin). The resulting test medium will contain nucleic acids in single-stranded form which can then be assayed according to the present hybridization method. Additionally, the nucleic acids can be fragmented specifically or nonspecifically in order to conduct a particular desired assay such as where point mutations are detected by specific endonuclease treatment followed by dual hybridization restriction (see for example, U.S. application Ser. No. 511,063, supra).

As is known in the art, various hybridization conditions can be employed in the assay. Typically, hybridization will proceed at slightly elevated temperatures, e.g., between about 35° and 75° C. and usually around 65° C., in a solution comprising buffer at pH between about 6 and 8 and with appropriate ionic strength (e.g., 5XSSC where 1XSSC=0.15M sodium chloride and 0.015M sodium citrate, pH 7.0) and optionally protein such as bovine serum albumin, and a denatured foreign DNA such as from calf thymus or salmon sperm. In cases where lower hybridization temperatures are desirable, hydrogen bonding reagents such as dimethylsulfoxide and formamide can be included. The degree of complementarity between the sample and probe strands required for hybridization to occur depends on the stringency of the conditions. Factors which determine stringency are known in the art.

Normally, the temperature conditions selected for hybridization will be incompatible with the binding of antibody reagent to formed hybrids and detection of the label response. Accordingly, any antibody reagent binding step and label detection step will proceed after completion of the hybridization step. The reaction mixture will usually be brought to a temperature in the range of from about 3° C. to about 40° C. and the binding and detection steps then performed. Dilution of the hybridization mixture prior to addition of antibody reagent is desirable when the salt and/or formamide concentrations are high enough to interfere significantly with the antibody reagent is desirable when the salt and/or formamide concentrations are high enough to interfere significantly with the antibody binding reaction. In the case of assays which involve the use of label binding partners or labeled antibody reagent to detect hybridization of the probe, the sequence of assay steps will generally proceed as follows. The hybridization reactions will be first accomplished with the test sample commonly having been pretreated as discussed above.

The present invention additionally provides a reagent system, i.e., reagent combination or means, comprising all of the essential elements required to conduct a desired assay method. The reagent system is presented in a commercially packaged form, as a composition or admixture where the compatibility of the reagents will allow, in a test device configuration, or more usually as a test kit, i.e., a packaged combination of one or more containers, devices, or the like holding the necessary reagents, and usually including written instructions for the performance of assays. Reagent systems of the present invention include all configurations and compositions for performing the various hybridization formats described herein.

A test kit form of the system can additionally include ancillary chemicals such as the components of the hybridization solution and denaturation agents capable of converting double-stranded nucleic acids in a test sample into single-stranded form. The kit can also include a container or containers to hold the above components.

Although some of the heretofore processes produce useful results, the methods either use a three component system or a kinetically slow procedure. The present invention is an improvement of the homogeneous method. The hybridization of the present invention is carried out with a two component system in solution and then the hybrid is separated by reaction with a solid substrate. The separation is carried out by a reactive site/reactive partner system. Preferably such reactive site in the probe or the test sample can be a binding site, such as a biotin or hapten moiety which is capable of specific non-covalent binding with a binding substance such as avidin or an antibody which serves as the reactive partner. The reactive partner is provided in an immobilized form such as attached to a solid support. Accordingly, after hybridization, the solution is contacted with the immobilized reactive partner to permit formation of a stable bond with the reactive site in the nucleic acid, the immobilized reactive partner is separated from the solution and either the resulting separated immobilized fraction or the remaining solution, or both, is assayed for the presence of the detection label.

One especially useful combination of reactive site and its immobilized reactive partner involves the avidin or streptavidin-biotin complement. Thus one of this pair is attached to the probe DNA or the sample and the other to a solid support, both done in known manner as described, for example, in patent application Ser. No. 513,932, filed July 14, 1983, now pending. Non-limiting examples for use as the solid support include "SEPHADEX" gel, agarose, nylon, polystyrene beads, cellulose beads, cellulose paper, nitrocellulose paper and plastic.

Preferably, the detection label is a detectable chemical group which can be radioactive, fluorescent, enzymatic or the like, and any of those of application Ser. No. 513,932, supra, is suitable.

The nucleic acids (test sample or the probe) are used as dilute aqueous solutions which can be combined with each other. By utilizing suitable conditions of ionic strength, pH and temperature, if the proper components are present, hybridization will occur very rapidly. Then the immobilized reactive partner is introduced and, after a suitable time to permit interaction of the reactive partner and reaction site, the immobile phase or fraction is removed, washed and the assay conducted, in known manner as described in application Ser. No. 511,063, supra.

The invention will now be described with reference to the drawing wherein like parts are designated by like reference numerals.

In the drawing, the nucleic acid 11 is reacted with a label or a reactive site 12 to form a labeled or reactive site-modified nucleic acid (P) 13. When a label 12 is for detection and when a reactive site is for separation, the test sample nucleic acid 21 is reacted with, respectively, a reactive site or label 22 to form a reactive site-modified or labeled nucleic acid (T) 23.

The products (P) 13 and (T) 23 are hybridized in aqueous solution. Then the resultant product (PT) 31 is separated by reaction with a solid substrate 32 which will form strong interaction with label or reactive site 12 or 22, as the case may be. After washing 33 to remove any unreacted nucleic acids, the extent of label is detected on the solid support containing moiety 33 or the amount of label in the remaining solution is determined. The detection can be done in the washings also. The type of label 12 and 22 can be interchanged, i.e., 11 can be labeled with 22 and 21 can be labeled with 12, without adversely affecting the process.

The invention will now be described with reference to the following non-limiting examples.

Example 1:

A known sample of pBR 322 DNA (commercially available from International Biotechnologic, Inc., New Haven, Conn., U.S.A.) is digested with pst I restriction enzyme for linearization. The linearized nucleic acid sample is dialyzed against 10 mM sodium borate buffer (pH 8). The concentration of, the solution is maintained at 1 µg/µl. To the DNA solution 4'-amino-methyl-4,5' dimethyl angelicin in 1:5 molar ratio (ligand: base pair) is added. The solution is irradiated at 346 nm for 30 minutes. The reacted nucleic acid (A) solution is dialyzed again against the same buffer to remove the unreacted ligand. The solution is then divided into two halves. One half is reacted with N-hydroxy suciinimido biotin by adding 10 times molar excess of, the reacting biotin derivative. The biotinylated pBR 322 (B) is purified by dialyzing against the same buffer.

The samples (A) and (B) are denatured by heating in a boiling water bath for 5 minutes, then chilling in ice.

Five aliquotes of sample (A) (denatured as above) ranging from 1 µg to 0.1 ng are placed separately in ice cooled test tubes. The volumes of the solution are made identical (1 ml) by adding borate buffer. To each test tube 1 µg equivalent (B) (10 µl in water) is added and are incubated at 65° C for 5 minutes, then they are chilled in ice. To these ice cooled solutions, 2 ml each of NHS-activated agarose, ("AFFIGEL-10", Biorad, Calif., U.S.A.) are added. The approximated volume of the gel is 200 µl. Incubation is conducted at 0° C. for 30 minutes.

This activated gel will covalently bind to (A) and to (A)(B) hybrid. Only the hybrid bound beads will show the presence of biotin.

The beads are washed at room temperature with borate buffer (2 times); then with borate buffer containing BSA (1 mg/ml), FITC labelled avidin is added and washed with the same buffer. The fluorescent beads are visually detected under a fluorescence microscope. Biotin detection is also done by adding a streptavidine-alkaline phosphate system available from Bethesda Research Laboratories, Md., U.S.A.

Example 2:

A prenatal test for alpha-thalassaemia

Example 2A

The background of, the disease and the preparation of the probe have been described by E. M. Rubin and Y. W. Kan, *The Lancet,* Jan. 12, 1985, page 75.

Instead of immobilizing the sample DNA onto nitrocellulose paper (as described by Rubin et al, supra) the nucleic acid sample is labelled photochemically with biotin as in (B) of Example 1. The probe is labelled photochemically with 4'-aminomethyl, 4,5' dimethyl angelicin as (A) in the Example 1. The hybridization and detection procedures are identical to that described in Example 1.

Example 2B

Example 2B was conducted in the same manner as Example 2A, with the following difference: The DNA sample is labeled with aminoangelicin as is described in Example 1 and the probe is labeled with biotin as is described in Example 1.

Example 3:

A Test for Microorganisms in a Sample

Step 1: Syntheis of Photolabelling Reagents:

Compounds 1 to 6, the formulas for which are as follows, were used for labelling nucleic acid samples:

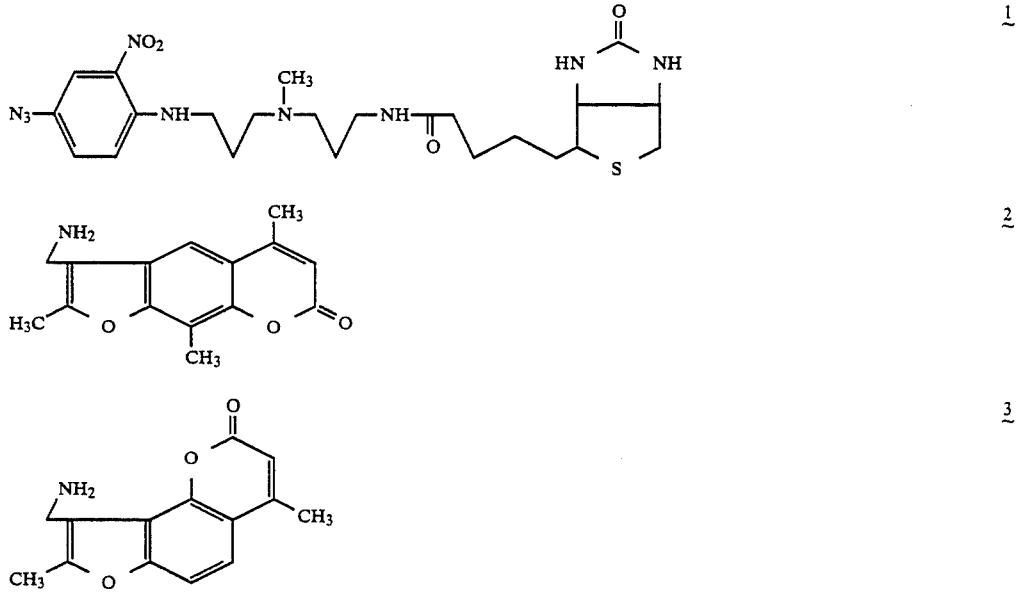

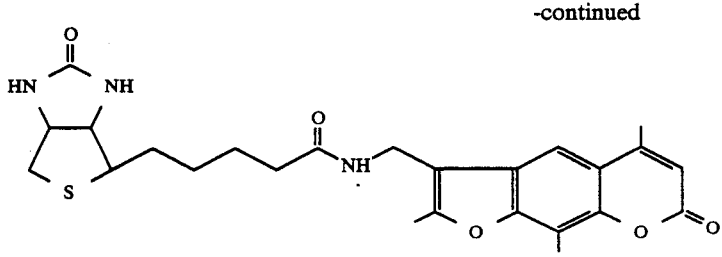

4

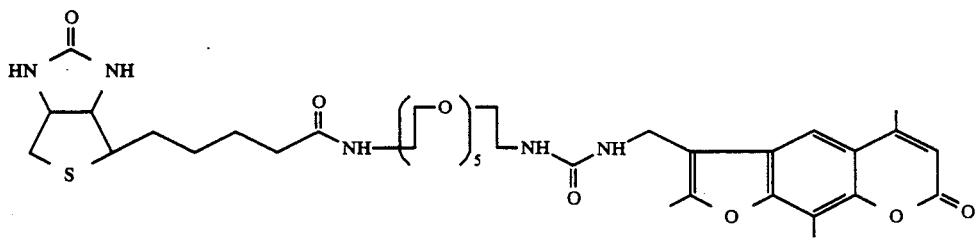

5

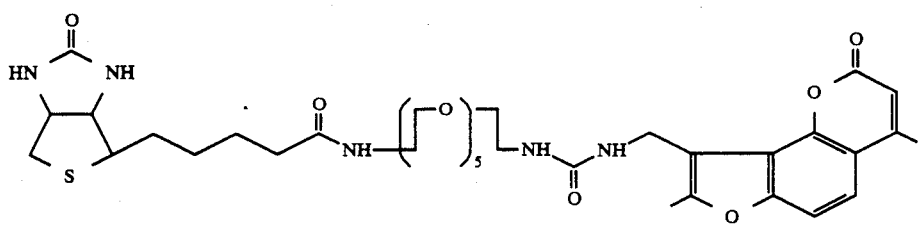

6

When compounds 2 and 3 were used, a second reaction with N-hydroxy succinimido biotin was carried out to link biotin to nucleic acids. Compound 1 was commercially available from BRESA, Australia. Compounds 2 and 3 have been described in U.S. Pat. No. 4,542,102. Compound 4 (4'Biotinylamido-4,5',8-trimethylpsoralen) was prepared as follows: A solution containing 166 mg of 4'-aminomethyl-4,5'-,8- trimethylpsoralen (0.65 mmol) and 110 ul of triethylamine (80 mg, 1.1 mmol) at 40° C. was treated with 275 mg of N-succinimidyl biotin (0.8 mmol). The resulting solution was stirred for 3 hours at 40° C. The reaction mixture was then evaporated onto $SiO_2$. flash-chromatographed on 60 g of $SiO_2$ (230–400 mesh) and then eluted with a 9:1 $CHCl_3$-$CH_3OH$ solvent mixture. The product was recrystallized from ethanol to give 101 mg of a white solid after drying at 55° C., 0.1 mm (32% yield). Analysis: Calculated for $CH_{25}H_{29}N_3O_5S.\frac{1}{2}H_2O$: C, 60.96, H, 6.14; N, 8.53. Found: C, 60.52; H, 6.01; N, 8.24.

Preparation of compounds 5 and 6 required 1-amino-17-N-(Biotinylamido)-3,6,9,12,15 pentaoxaheptadecane. This was achieved in four stages, namely as follows:
(1) 3,6,9,12,15 pentaoxaheptadecane (x)-1,17-diol ditosylate was synthesized.
(2) 1,17-dipthalimido derivative of (x) was prepared.
(3) 1,17-diamino derivative of (x) was prepared.
(4) 1 amino, 17-biotinylamido derivative of (x) was prepared.

Preparation of 3,6,9,12,15-Pentaoxaheptadecane-17,diol ditosylate:

To a stirred solution containing 50 g of hexaethylene glycol (0.177 mol) and 64 ml of triethylamine (39.36 g, 0.389 mol) in 400 ml of $CH_2Cl_2$ at 0° C. was added dropwise a solution containing 73.91 g of p-toluenesulfonyl chloride (0.389 mol) in 400 ml of $CH_2Cl_2$ over a 2.5 hour period. The reaction mixture was then stirred for 1 hour at 0° C. and then allowed to warm to ambient temperature for 44 hours. The mixture was then filtered and the filtrate concentrated in vacuo. The resulting heterogeneous residue was suspended in 500 ml of ethyl acetate and filtered. The filtrate was then concentrated in vacuo to a yellow oil which was triturated eight times with 250 ml portions of warm hexane to remove unreacted p-toluenesulfonyl chloride. The resulting oil was then concentrated under high vacuum to give 108.12 g of a yellow oil (quantitative yield).

Analysis Calculated for $C_{26}H_{38}O_{11}S_2$:
Calculated: C, 52.87; H, 6.48.
Found: C, 52.56; H. 6.39.

Preparation of 1,17-Diphthalimido-3,6,9,12,15-pentaoxahepta decane

A stirred suspension containing 108 g of 3,6,9,12,15-pentaoxaheptadecane-1,17-diol ditosylate (0.183 mol), 74.57 g of potassium phthalimide (0.403 mol), and 700 ml of dimethylacetamide was heated at 160°–170° C. for 2 hours and was then allowed to cool to room temperature. The precipitate was filtered and washed with water and acetone to give 53.05 g of product as a white powder which was dried at 55° C. (0.1 mm). mp 124°–126° C.

A second crop of product was obtained from the dimethylacetamide filtrate by evaporation in vacuo and successively washing the resulting precipitate with ethyl acetate, water, and acetone. The resulting white powder was dried at 55° C. (0.1 mm) to give an additional 9.7 g of product. mp 124.5°–126.5°. The combined yield of product was 62.82 g (68% yield).

Analysis: (For first crop)
Calculated for $C_{28}H_{32}N_2O_9.\frac{1}{2}H_2O$:
Calculated: C, 61.19; H, 6.05; N, 5.09.
Found C, 61.08; H, 6.15; N, 5.05.
(For second crop)
Calculated for $C_{28}H_{32}N_2O_9$.

Calculated: C, 62.21; H, 5.97; N, 5.18.
Found: C, 61.78; H, 6.15; N, 5.13.

Preparation of
1,17-Diamino-3,6,9,12,15-Pentaoxaheptadecane

A solution containing 60 g of 1,17-diphthalimido-3,6,9,12,15 - pentaoxaheptadecane (0.118 mol), 14.8 g of hydrazine hydrate (0.296 mol) and 500 ml of ethanol were heated with mechanical stirring in a 100° C. oil bath for 3 hours. The mixture was then allowed to cool and was then filtered. The filter cake was washed four times with 300 ml portions of ethanol. The combined filtrates were concentrated to give 32.35 g of a yellow opaque glassy oil. Evaporative distillation at 150°-200° C. (0.01 mm) gave 22.82 g of a light yellow oil (69% yield).

Analysis: For $C_{12}H_{28}N_2O_5.\frac{1}{2}H_2O$:
Calculated: C, 49.80; H, 10.10; N, 9.68.
Found: C, 50.36; H, 9.58; N, 9.38.
(W. Kern, S. Iwabachi, H. Sato, and V. Bohmer, *Makrol. Chem.*, 180, 2539 (1979)).

Preparation of
1-Amino-17-N-(Biotinylamido)-3,6,9,12,15-pentaoxaheptadecane

A solution containing 7.2 g of 1,17-diamino-3,6,9,12,15-pentaoxaheptadecane (25 mmol) in 75 ml of DMF under an argon atmosphere was treated with 3.41 g of N-succinimidyl biotin (10 mmol) added in portions over 1.0 hour. The resulting solution was stirred for 4 hours at ambient temperature. TLC ($SiO_2$, 70:10.1 $CHCl_3$-$CH_3OH$-conc. $NH_4OH$) visualized by dimethylaminocinnamaldehyde spray reagent showed excellent conversion to a new product (Rf=0.18). The reaction mixture was divided in half and each half was absorbed onto $SiO_2$ and flash-chromatographed on 500 g of $SiO_2$-60 (230=400 mesh) using a 70:10.1 $CHCl_3$-$Ch_3OH$-conc. $NH_4OH$ solvent mixture. Fractions containing the product were pooled and concentrated to give 2.42 g of a gelatinous, waxy solid. The product was precipitated as a solid from isopropanol-ether, washed with hexane, and dried at 55° C. (0.1 mm) to give 1.761 g of a white powder (35% yield).

Analysis: Calculated for $C_{22}H_{42}N_4O_7S.3/2\ H_2O$:
Calculated: C, 49.51; H, 8.50; N, 10.49.
Found: C, 49.59; H, 8.13; N, 10.39.
Mass Spectrum (FAB) m/e: 507.3 (M+1, 56%)

Preparation of 4'-(Biotinyl-PEG)-Trioxsalen (Compound 5)

A solution of 380 mg of 1-Amino-17-N-(Biotinyl-amido)-3,6,9,12,15-pentaoxaheptadecane (0.75 mmol) in 3 ml of DMF under an argon atmosphere was treated with 146 mg of N,N-carbonyldiimidazole (0.9 mmol). The resulting solution was stirred for 2.5 hours. TLC ($SiO2$, 4:1 $CHCl_3$-$CH_3OH$, visualization with dimethylaminocinnamaldehyde spray reagent) indicated a complete conversion of biotinylamine (Rf=0.1) to imidazourea (Rf=0.5). The reaction mixture was then treated with 193 mg of 4'-aminomethyl-4',5',8-trimethylpsoralen (0.75 mmol) and 2.7 µl of triethylamine (1.57 mmol). The resulting mixture was then heated at 60° C. overnight. TLC ($SiO_2$, 4:1 $CHCl_3$-$CH_3OH$) indicated conversion of imidazolide to a new product (Rf=0.52) which is both uv fluorescent and tested positive with the dimethylamino-cinnamaldehyde spray reagent.

The solvents were removed in vacuo to a gelatinous oil, which was dissolved in $CH_3OH$ and absorbed onto $SiO_2$. The impregnated solid was then flash-chromatographed on 60 g of $SiO_2$-60 (230–400 mesh) using a 9:1 $CHCl_3$-$CH_3OH$ solvent mixture. Fractions containing the partially purified product were pooled and then rechromatographed using 60 g of $SiO_2$ eluted with the same solvent system.

mp: decomposed slowly 129.5° C. to 149.5° C.
Analysis Calculated for $C_{38}H_{55}N_5O_{11}S.H_2O$:
Calculated: C, 56.49, H, 7.11; N, 8.67
Found: C, 56,58; H, 7.16; N, 8.53.
Mass Spectrum (FAB) m/e: 790 (M+1, 30%).

Preparation of 4'-Biotinyl-PEG)-4,5'-dimethylangelicin (Compound 6)

A solution of 203 mg of 1-amino-17-N-(biotinyl-amido)-3,6,9,12,15-pentaoxaheptadecane (0.4 mmol) in 1 ml of DMF under an argon atmosphere was treated with 78 mg of N,N-carbonyldimidazole (0.48 mmol). The resulting mixture was stirred for 4 hours and was then treated with 55 mg of 4'aminomethyl-4,5' dimethylingelicin hydrochloride (F. Dall'Acqua, D. Vedaldi, S. Caffieri, A. Guiotto, P. Rodighiero, F. Baccichetti, F. Carlassare and F. Bordin, *J. Med. Chem.*, 24 178 (1981)) (0.2 mmol), 140 µl of diisopropylethylamine and 100 µl of DMF. The resulting mixture was stirred overnight at 50° C. The mixture was then evaporated onto $SiO_2$ in vacuo and the impregnated solid flash chromatographed on 60 g of $SiO_2$ (230–400 mesh) and was then eluted with 1.5 l of 7% $CH_3OH(CHCl_3)$ followed by 1 liter of 10% $CH_3OH(CHCl_3)$ Fractions containing the product were pooled and concentrated to give 72 mg of a glassy solid (47% yield).

Step 2: Processing of a Test Sample for Cellular DNA Labelling

Samples of urine, for example (although the following can equally apply to suspensions of material from gonorrhoea-suspect swabs, from meningitis-suspect cerebrospinal fluid, from contamination-suspect water samples, etc.), are centrifuged or filtered to wash and concentrate any bacteria in the sample. The bacteria are then lysed by exposure to either (i) 2 mg/ml lysozyme or lysostaphin then exposure to approximately 90° C. heat, (ii) 0.2 N NaOH, or (iii) 1% Na dodecyl sulfate. After (ii) NaOH, the cell lysate solution is neutralized before labelling; after (iii) detergent lysis, DNA labelling is preceded by removal of the SDS with 0.5 M K acetate on ice. Compounds 1 to 6 should be able to permeate intact cells so that DNA labelling can be accomplished before cell lysis. This in situ labelling simplifies the extraction procedure, as alkaline or detergent lysates can be incorporated directly into a hybridization solution. It is also surprisingly possible to label whole cells before any lysis by mixing the whole cells with the labelling reagent and conducting irradiation.

Prior to hybridization the labelled sample is denatured, and it should also preferably be reduced to short single stranded lengths to facilitate specific annealing with the appropriate unlabelled probe DNA. Methods of denaturation are known in the art. These methods include treatment with sodium hydroxide, organic solvent, heating, acid treatment and combinations thereof. Fragmentation can be accomplished in a controlled way be heating the DNA to approximately 80° C. in NaOH for a determined length of time, and this, of course, also denatures the DNA.

Step 3: Labelling of the Products of Step 2

(i) A test sample of about 10 ml urine will contain $10^4$ or more infectious agents. After separation by centrifugation and washing, the pretreated cell lysate (step 2) is resuspended in 0.2 ml 10 mM sodium borate buffer (pH approximately 8). To this suspension, 10 μg of photolabelling reagent dissolved in ethanol (10 mg/ml), is added and mixed by shaking on a vortex mixer. The mixture is then irradiated at 365 nm for 30 minutes with a UVGL 25 device at its long wavelength setting. The UVGL device is sold by UVP Inc., 5100 Walnut Grove Avenue, P.O. Box 1501, San Gabriel, Calif. 91778, U.S.A.

(ii) The sample can also be labelled with N-(4-azido-2-nitrophenyl)-N'-(N-d-biotinyl-3-amino-propyl)- N'-methyl-1,3-propanediamine (commercially available from BRESA, G.P.O. Box 498, Adelaide, South Australia 5001, Australia), following the procedure described by Forster et al, *Nucleic Acid Res.*, 13, 745 (1985), for DNA.

(iii) When unlysed cells are used, the cell suspension in 0.2 ml 10 mM borate is incubated with the photoreagent for 1 hour prior to irradiation.

Step 4: Hybridization and Detection of the Products of Steps 2 and 3

Hybridization and detection of the products of steps 2 and 3 are carried out by the method described in Example 1.

It will be understood that the specification and examples are illustrative but not limitative of the present invention and that other embodiments within the spirit and scope of the invention will suggest themselves to those skilled in the art.

What is claimed is:

1. A process for determining the presence of a particular nucleic acid sequence in a sample containing cells comprising
   (a) chemically modifying nucleic acids in an unpurified sample, said sample consisting essentially of whole cells, said whole cells being lysed during the process, cell lysates and mixtures thereof, either to introduce a label or a reactive site, wherein the chemical modification of the sample nucleic acids to introduce said label or said reactive site is accomplished by reaction with a photochemical reagent comprising said label or reactive site, respectively,
   (b) conducting hybridization,
   (c) contacting under hybridization conditions the chemically modified sample nucleic acids with a hybridizable nucleic acid probe which either, when the sample nucleic acids have been modified to introduce a label, includes a reactive site, or when the sample nucleic acids have been modified to introduce a reactive site, is labeled,
   (d) contacting the solution resulting from step (c) with an immobilized form of a reactive site on the sample nucleic acids or the probe, respectively,
   (e) separating the resulting immobilized fraction from the remaining solution, and
   (f) determining the presence of the label in the separated immobilized fraction or a decrease in the label in the remaining solution.

2. A process according to claim 1, wherein said photochemically reactive reagent is a nucleic acid binding ligand.

3. A process according to claim 1, wherein the immobilized form of the reactive partner comprises a solid support to which the reactive group is attached.

4. A process according to claim 1, wherein the reactive site is a binding site capable of specific noncovalent binding.

5. A process according to claim 4, wherein the binding site is biotin or a hapten and wherein the immobilized reactive partner is an immobilized form of avidin or an anti-hapten antibody reagent, respectively.

6. A process according to claim 1, wherein the label is selected from the group consisting of an enzymatically active group, a fluorescer, a chromophore, a luminescer, a specifically bindable ligand and a radioisotope.

7. A process according to claim 1, wherein the label is a specifically bindable ligand and its presence is determined by binding with a labeled binding partner therefor.

8. A process according to claim 7, wherein the ligand is biotin or a hapten and the binding partner therefor is avidin or an anti-hapten antibody reagent, respectively.

9. A process according to claim 1, wherein the particular sequence of interest is characteristic of the presence or absence of a particular genetic disorder.

10. A process according to claim 9, wherein the genetic disorder is sickle cell anemia.

11. A process according to claim 1, wherein the test sample nucleic acids are chemically modified to introduce a label in step (a) and the resulting labeled sample nucleic acids are contacted in step (b) with a probe that carries a reactive site.

12. A process according to claim 1, wherein the test sample nucleic acids are chemically modified to introduce a reactive site in step (a) and the resulting reactive site-modified sample nucleic acids are contacted in step (b) with a labeled probe.

13. A process according to claim 1, wherein the probe has a concentration that is greater than that of the sample.

14. A process according to claim 13, wherein the concentration of the probe is in excess of the sample by at least 1,000 times.

15. A process according to claim 1, wherein the cells are lysed.

* * * * *